(12) United States Patent
Verstreken et al.

(10) Patent No.: US 10,390,840 B2
(45) Date of Patent: Aug. 27, 2019

(54) ACCESSORY FOR OSTEOTOMY

(71) Applicant: Biomet Manufacturing, LLC, Warsaw, IN (US)

(72) Inventors: Frederik Marie Andre Jozef Verstreken, Schoten (BE); Xavier Martin Yves Deklerck, Oostkamp (BE)

(73) Assignee: Biomet Manufacturing, LLC, Warsaw, IN (US)

( * ) Notice: Subject to any disclaimer, the term of this patent is extended or adjusted under 35 U.S.C. 154(b) by 394 days.

(21) Appl. No.: 15/116,427

(22) PCT Filed: Feb. 16, 2015

(86) PCT No.: PCT/BE2015/000004
§ 371 (c)(1),
(2) Date: Aug. 3, 2016

(87) PCT Pub. No.: WO2015/127515
PCT Pub. Date: Sep. 3, 2015

(65) Prior Publication Data
US 2017/0007267 A1    Jan. 12, 2017

(30) Foreign Application Priority Data

Feb. 26, 2014    (BE) .................................. 2014/0125

(51) Int. Cl.
*A61B 17/15*    (2006.01)
*A61B 17/17*    (2006.01)
*A61B 17/80*    (2006.01)

(52) U.S. Cl.
CPC ........ *A61B 17/151* (2013.01); *A61B 17/1739* (2013.01); *A61B 17/8019* (2013.01); *A61B 17/8061* (2013.01)

(58) Field of Classification Search
CPC ............................ A61B 17/151; A61B 17/152
See application file for complete search history.

(56) References Cited

U.S. PATENT DOCUMENTS 4,565,191 A * 1/1986 Slocum ................ A61B 17/152
606/87
4,929,247 A * 5/1990 Rayhack ............ A61B 17/8019
606/105

(Continued)

FOREIGN PATENT DOCUMENTS

| CN | 102753109 | 10/2012 |
| CN | 102791211 | 11/2012 |

(Continued)

OTHER PUBLICATIONS

"European Application Serial No. 15723822.1, Response filed Jun. 1, 2017 to Communication pursuant to Rules 161(1) and 162 EPC dated Nov. 22, 2016", 13 pgs.

(Continued)

*Primary Examiner* — David W Bates
(74) *Attorney, Agent, or Firm* — Schwegman Lundberg & Woessner, P.A.

(57) ABSTRACT

Set suitable for use in a bone-shortening osteotomy of a predetermined distance, the set comprising: an implant (1) with threaded holes (8); an accessory (2) with successively a first segment (5), a second segment (6) and a third segment (7); wherein the first segment comprises first threaded holes (9) and wherein the third segment comprises second threaded holes (9), and wherein the second segment comprises two guides (10) which are each adapted to guide a saw blade (17) so that the osteotomy of predetermined distance (d) can be performed via the two guides.

15 Claims, 3 Drawing Sheets

(56) References Cited

U.S. PATENT DOCUMENTS

| | | | |
|---|---|---|---|
| 5,042,983 A * | 8/1991 | Rayhack | A61B 17/15 606/53 |
| 5,176,685 A * | 1/1993 | Rayhack | A61B 17/15 606/105 |
| 6,007,535 A * | 12/1999 | Rayhack | A61B 17/15 606/105 |
| 6,206,882 B1 * | 3/2001 | Cohen | A61B 17/7059 606/283 |
| 8,652,142 B2 * | 2/2014 | Geissler | A61B 17/15 606/87 |
| 2005/0277941 A1 * | 12/2005 | Trumble | A61B 17/15 606/79 |
| 2007/0276383 A1 * | 11/2007 | Rayhack | A61B 17/15 606/86 B |
| 2010/0168799 A1 * | 7/2010 | Schumer | A61B 17/151 606/286 |
| 2012/0123484 A1 | 5/2012 | Lietz et al. | |
| 2015/0245858 A1 * | 9/2015 | Weiner | A61B 17/15 606/281 |
| 2016/0030066 A1 * | 2/2016 | Cunliffe | A61B 17/151 606/281 |
| 2016/0235454 A1 * | 8/2016 | Treace | A61B 17/8061 |

FOREIGN PATENT DOCUMENTS

| | | |
|---|---|---|
| CN | 106132320 A | 11/2016 |
| EP | 2019637 | 9/2013 |
| GB | 2334214 | 8/1999 |
| JP | 2017510332 A | 4/2017 |
| JP | 6445579 | 12/2018 |
| WO | WO-2013156545 A1 | 10/2013 |
| WO | WO-2015127515 A2 | 9/2015 |
| WO | WO-2015127515 A3 | 9/2015 |

OTHER PUBLICATIONS

"International Application Serial No. PCT/BE2015/000004, International Preliminary Report on Patentability dated Sep. 9, 2016", 10 pgs.

"International Application Serial No. PCT/BE2015/000004, International Search Report dated Sep. 16, 2015", 5 pgs.

"International Application Serial No. PCT/BE2015/000004, Written Opinion dated Sep. 16, 2015", 6 pgs.

"Chinese Application Serial No. 201580016647.6, Office Action dated Nov. 26, 2018", w English translation, 8 pgs.

"Australian Application Serial No. 2015222700, First Examination Report dated Jun. 28, 2018", 4 pgs.

Chinese Application Serial No. 201580016647.6, Response filed Jul. 13, 2018 to Office Action dated Mar. 2, 2018, W/English Translated Claims, 12 pgs.

"Chinese Application Serial No. 201580016647.6, Office Action dated Mar. 2, 2018", W English Translation, 12 pgs.

"Chinese Application Serial No. 201580016647.6, Response Filed Jan. 28, 2019 to Office Action dated Nov. 26, 2018", (W/ English Claims), 6 pgs.

"Canadian Application Serial No. 2,940,580, Examiners Rule 30(2) Requisition dated Feb. 18, 2019", 3 pgs.

"Canadian Application Serial No. 2,940,580, Response filed Mar. 6, 2019 to Examiners Rule 30(2) Requisition dated Feb. 18, 2019", 4 pgs.

"Chinese Application Serial No. 201580016647.6, Office Action dated Jun. 3, 2019", w English translation, 8 pgs.

* cited by examiner

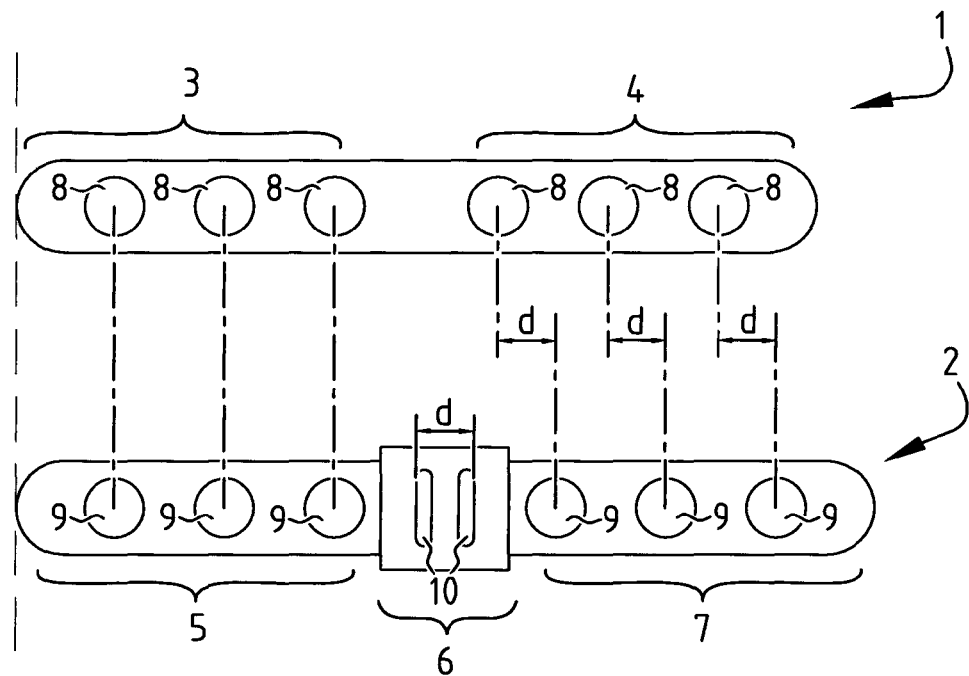
FIG. 1
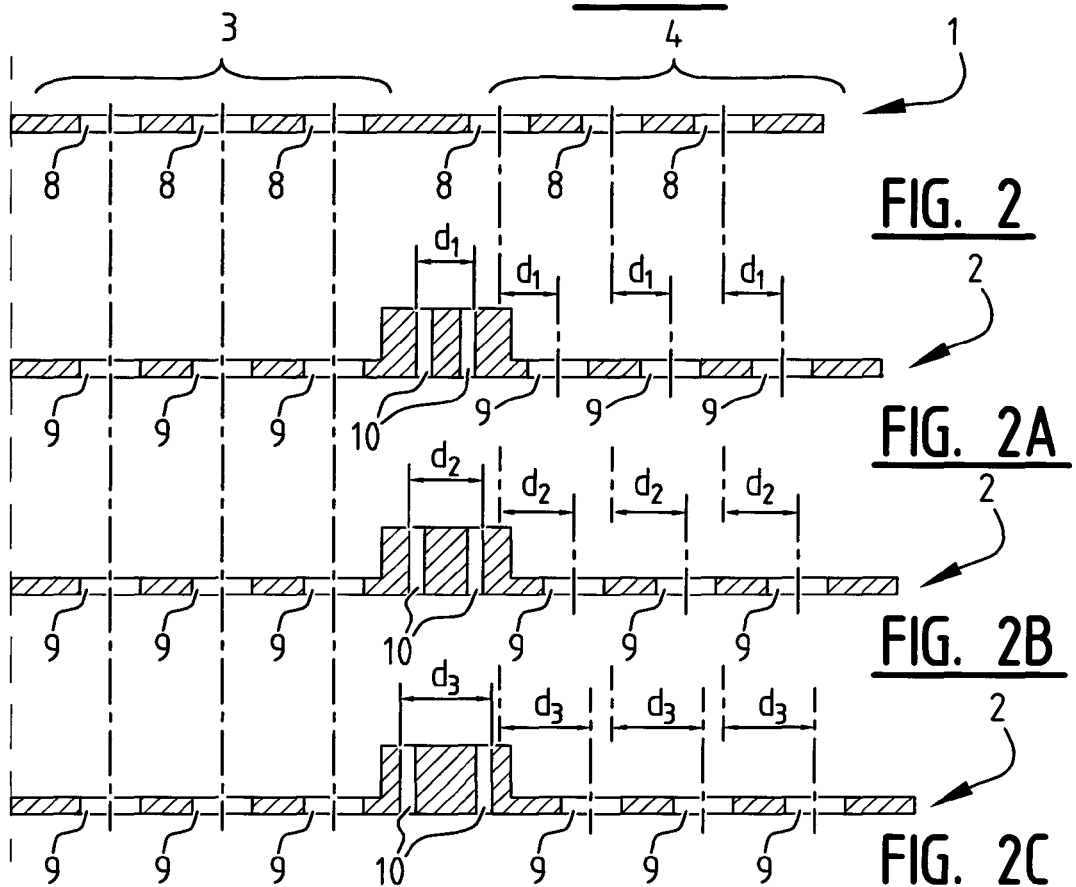
FIG. 2
FIG. 2A
FIG. 2B
FIG. 2C

ACCESSORY FOR OSTEOTOMY

CLAIM OF PRIORITY

This application is a U.S. National Stage Filing under 35 U.S.C. 371 from International Application No. PCT/BE2015/000004, filed on 16 Feb. 2015, and published as WO 2015/127515 A2 on 3 Sep. 2015, which claims the benefit to Belgian Application No. 2014/0125, filed on 26 Feb. 2014 the benefit of priority of each of which is claimed hereby, and each of which are incorporated by reference herein in its entirety.

The invention relates to a set suitable for use in a bone-shortening osteotomy of a predetermined distance.

Ulnar abutment is a condition of the wrist caused by chronic strain on the part of the wrist adjacent to the ulna, which may result in inflammation and degenerative changes to the ligaments and cartilage. A bone-shortening osteotomy is a surgical treatment for this problem.

A bone-shortening osteotomy of the ulna is a surgical procedure wherein an incision is made in the lower arm of the patient. The ulna is exposed via this incision. The surgeon then saws through the ulna in order to shorten the ulna. The surgeon preferably saws through the ulna at two locations for this purpose, wherein the two saw cuts have an intermediate spacing corresponding to the desired shortening of the ulna. The bone segment between the two saw cuts is removed and the two parts of the ulna are positioned and secured relative to each other by means of an implant. This implant is typically a bone-shortening plate with threaded holes, wherein screws are placed through the threaded holes and into the bone. The implant is typically manufactured from stainless steel or titanium, and is therefore relatively expensive. After securing of the implant the lower arm wound is closed. The implant typically remains for at least several months in the arm of the patient such that the two parts (with the two saw cuts) of the ulna can fuse. Once the two parts of the ulna have fused, the implant can optionally be removed.

It is an object of the invention to provide a set for performing a bone-shortening osteotomy of a predetermined distance with which a surgeon can perform the osteotomy with a minimum number of operational steps and with maximum precision.

The invention provides for this purpose a set suitable for use in a bone-shortening osteotomy of a predetermined distance, the set comprising an implant with a distal segment and a proximal segment, wherein the distal segment comprises at least two distal threaded holes and wherein the proximal segment comprises at least two proximal threaded holes; an accessory (guide) comprising successively a first segment, a second segment and a third segment, wherein the first segment comprises first threaded holes and wherein the third segment comprises second threaded holes, and wherein the second segment comprises two guides which are each adapted to guide a saw blade so that the osteotomy of predetermined distance can be performed via the two guides, wherein the first threaded holes and the second threaded holes respectively correspond to the at least two distal threaded holes and the at least two proximal threaded holes, with an intermediate spacing between first and second threaded holes which is equal to the sum of said predetermined distance and a corresponding intermediate spacing between distal and proximal threaded holes, and wherein the first segment and the third segment have the same shape, at least at the position of the threaded holes, as respectively the distal segment and proximal segment.

The set according to the invention comprises two elements, i.e. the implant and the accessory. The accessory is formed here to assist the surgeon during shortening of the ulna. Because the accessory is used to shorten the ulna, the implant (which is typically expensive because it is formed from titanium) can be a standard implant. Standard implant is defined here as an implant wherein only those elements and forms are provided which are necessary for holding the two parts of the ulna together. Because the implant is a standard implant it can be manufactured in simple manner and comprises no superfluous/unnecessary material. Nor does the implant then need to be modified to the predetermined distance. The accessory is provided in order to be used by the surgeon during shortening of the ulna. The accessory therefore comprises two guides for guiding a saw blade. A surgeon can shorten the ulna by the predetermined distance via the two guides. These guides allow the surgeon to saw in very precise manner into the ulna. This allows shortening of the ulna by a predetermined distance (wherein the tolerance in the predetermined distance is very small). This further allows the two saw cuts made in the ulna to be sawn neatly parallel. The two parts of the ulna can hereby connect closely together when positioned, whereby the ulna can recover quickly and strongly (because the two parts fuse). The specific construction of the accessory, and particularly the similarities between the accessory and the implant (holes which correspond), have the following advantages. Because the holes in the first segment of the accessory correspond to the distal threaded holes of the implant, because the holes in the third segment of the accessory correspond to the threaded holes of the proximal segment of the implant and because the intermediate spacing between the first holes and the second holes of the accessory is equal to the sum of the predetermined distance and the intermediate spacing between the distal and proximal threaded holes of the implant, holes can be drilled in the bone at the moment the accessory is placed (and even before shortening of the ulna). These drilled holes can then be used at a later stage to secure the implant (after shortening of the ulna). Because the first segment and the third segment of the accessory have the same shape, at least at the position of the threaded holes, as respectively the distal segment and the proximal segment, a further advantage is obtained. In order to place a screw through a threaded hole and into a bone, the screw must have a length adapted to the depth of the threaded hole and the length of the hole through the bone. Before placing a screw a surgeon will therefore always measure the hole in the threaded hole in order to select a screw with a length suitable for use in the hole in question. Because the accessory has the same shape as the implant at the position of the threaded holes, the holes can be measured once the accessory has been placed and screws can be selected while the accessory is being placed. After the accessory has been removed and the implant has been placed, these screws can then be used directly, without the surgeon having to re-measure the holes. This allows a surgeon to perform an ulnar shortening in a highly efficient manner. This is because the surgeon can perform all critical steps (drilling the threaded holes, measuring the threaded holes, selecting the screws, sawing the bone) by means of the accessory. When the accessory is removed, all that remains is to secure the implant using the selected screws. The above shows that a bone-shortening osteotomy can be performed efficiently, quickly and precisely via a set according to the invention. A further advantage is that a standard bone-shortening plate can be used as implant for securing the two parts of the bone relative to each other, which is cheaper.

The whole first segment preferably has the same shape as the distal segment, and the whole third segment has the same shape as the proximal segment. By giving the first segment and the second segment the same shape as respectively the distal segment and the proximal segment the surgeon already gains a visual impression when placing the accessory of how the implant will be placed relative to the bone in a final position. A further advantage is that drilling of the holes and measuring of the drilled holes is even simpler via the accessory when the whole first and third segments of the accessory have the same shape as the distal and proximal segments.

'Have the same shape' is preferably specified as having substantially the same thickness. Have the same shape is more preferably specified as having an outer surface of the same shape. This defines the phrase 'have the same shape'. By defining the term 'have the same shape' it becomes unambiguously clear from the claim that the accessory has the same thickness as the implant, at least at the position of the threaded holes. It also becomes unambiguously clear that the accessory has an outer surface which has the same shape as the outer surface of the implant, at least at the position of the threaded holes.

'Correspond' is preferably specified as having a position relative to each other which is the same. This defines the term 'correspond'. The first threaded holes in the first segment of the accessory have a position relative to each other the same as that of the distal threaded holes. The second threaded holes in the third segment of the accessory have a position relative to each other the same as that of the proximal threaded holes.

Each guide is preferably formed as a channel substantially defined by two surfaces which extend parallel and between which the saw blade can move in order to be guided thereby in a sawing position and in a sawing direction. When a saw blade is positioned in a channel defined by two surfaces, the saw cut will typically extend parallel and in the same plane as the channel. The two surfaces typically lie at a distance relative to each other which is equal to or slightly greater than the thickness of the saw blade. The saw blade can thus be positioned in a sawing position and a sawing direction in the channel. The finally obtained saw cut is predetermined by fixing the sawing position and the sawing direction. The surgeon can in this way make a saw cut in the bone by means of the guides, wherein the position and the direction of the saw cut is wholly predetermined. Because each of the two guides is formed in this way, it will be possible to perform two saw cuts in precise manner, whereby the distance of the osteotomy can be precisely predetermined. The position of the two saw cuts relative to each other can also be precisely determined such that positioning of the two parts of the bone against each other (after shortening) is simple because the sawn ends fit neatly against each other (because they have been sawn precisely parallel).

The distal segment and the proximal segment preferably each comprise an opening for a Kirschner wire, and the first segment and the third segment each comprise a corresponding opening. The Kirschner wire openings are more preferably located at the position of the outer ends of the accessory. The threaded holes/holes of the implant/accessory further preferably lie in line with the Kirschner wire openings. Kirschner wires are often used in surgery to position accessories and/or implants relative to a bone. Providing corresponding Kirschner wire openings in accessory and in implant makes it possible to position the accessory by means of Kirschner wires, which Kirschner wires remain connected to the bone when the accessory is removed from the bone, and after which the implant can be positioned relative to the bone by means of these Kirschner wires already present in the bone. The Kirschner wires will further facilitate handling of the sawn-through bone (after removal of the accessory). In practice the accessory is fixed relative to the bone with at least two, but sometimes more, Kirschner wires. In order to make this possible a plurality of openings are preferably present in the accessory. The Kirschner wires on both outer ends of the accessory have the significant advantage that they assist in correct positioning of the accessory, and so also of the implant afterwards relative to the bone. If the accessory is correctly placed (correctly positioned) centrally on the bone, surgeons will become aware of this during insertion of the Kirschner wire on the basis of the resistance during drilling of the Kirschner wire opening, i.e. the resistance during drilling through hard bone (first cortex: hard bone), then less resistance (cancellous bone) and then resistance once again (second cortex: hard bone). It is proposed here in a preferred embodiment to provide a visual marking on the Kirschner wires at about 20 mm, making it possible to check how deeply the Kirschner wire has been placed into the bone, this being an additional check of the correct position thereof. If the Kirschner wires are placed correctly on the two outer ends of the accessory, it will automatically also be possible to drill all threaded holes correctly, because the accessory is then positioned correctly. This is the case when the threaded holes lie in one line, but also when the threaded holes are offset (which provides a stronger biomechanical fixation).

The Kirschner wires which are placed and for which a corresponding opening is provided in the implant remain in place after removal of the accessory, after which the implant is slid thereover so that the bone fragments already come to lie substantially in the correct position. If an implant is used without (corresponding) opening for Kirschner wires, the Kirschner wires which have been used for fixation of the accessory cannot remain in place. When according to an embodiment four holes for Kirschner wires are present in the implant, this will facilitate the temporary positioning of the implant and the bone fragments. Arranging the screws then provides for further improvement of the relative position of the bone fragments by compressing the bone fragments against each other. The function of the additional Kirschner wires (as described in the embodiment above) is to fix the accessory while the saw cuts are made as alternative to temporary placing of screws through the accessory. The accessory can after all become unstable during sawing when a saw cut is made if there is only one fixation on each side of the saw cut. An additional Kirschner wire can thus either be placed on each side of the saw cut or a screw can be temporarily placed on each side of the saw cut, or, as further alternative, the saw cuts can be incompletely made, after which the saw cuts are completed after removal of the accessory.

The set is preferably suitable for use in a bone-shortening osteotomy of a first predetermined distance and suitable for use in a bone-shortening osteotomy of a second predetermined distance, wherein the set comprises a further accessory formed similarly to the accessory, and wherein the accessory is adapted for the first predetermined distance and wherein the further accessory is adapted for the second predetermined distance. In such a configuration the set according to the invention comprises at least three elements, being one implant and at least two accessories. Each accessory is adapted here for a bone-shortening osteotomy of a predetermined distance. The first accessory can for instance be provided for the purpose of performing an osteotomy of 3 mm and the second accessory can be provided for the purpose of performing an osteotomy of 5 mm. The surgeon can select from such a set the accessory which is adapted for osteotomy of a predetermined distance which is suitable for the patient. When in the example above an osteotomy of 3 mm must be performed, the first accessory will be selected. When an osteotomy of 5 mm must be performed, the second accessory will be selected. The two accessories are adapted to the implant so as to have the above described advantages. Although an example has been given wherein one implant and two accessories are provided, it will be apparent that a plurality of accessories can be provided for a plurality of osteotomy distances. The implant remains standard here (i.e. of simple form), while an osteotomy of different distances can nevertheless be performed via the set of the invention. The set according to the invention in this way increases the freedom of the surgeon when performing the osteotomy.

The invention further relates to a method for performing a bone-shortening osteotomy of a predetermined distance, wherein the method is performed using a set according to the invention and wherein the method comprises of:

positioning an accessory from the set relative to the bone, the accessory comprising threaded holes and guides for guiding a saw;

wherein, after positioning of the accessory, the method comprises of:

drilling holes in the bone through the threaded holes;
measuring each of the drilled holes in order to select for each of the holes a screw with a length suitable for fixedly screwing the accessory onto the bone;
at least partially securing the accessory to the bone;
sawing the bone while making use of the guides;

after which the method comprises of removing the accessory and subsequently placing an implant from the set and fixedly screwing the implant making use of the respective selected screws.

Because the proximal segment and the distal segment of the implant have the same shape as respectively the first segment and the third segment of the accessory a very simple and accurate method is obtained for performing a bone-shortening osteotomy. In the method the accessory is placed first. Following placing of the accessory all further critical steps are performed by means of the accessory. This means that the bone is sawn, the threaded holes are drilled and the screws are selected by measuring the threaded holes. The sequence of performing these critical steps is not essential, although the bone is preferably sawn only after the holes have been drilled and measured. Once all these critical steps have been performed making use of the accessory, the accessory is removed, the implant is positioned and secured. Because the holes have already been pre-drilled in the bone and the screws have already been selected, the step of fixedly screwing the implant comprises no difficult steps. An osteotomy can therefore be performed in reliable and efficient manner according to the method of the invention which ensues from the specific construction of the set according to the invention.

The accessory is preferably positioned using Kirschner wires which are placed in the bone and which extend through Kirschner wire openings of the accessory. Kirschner wires are often used to position accessories and/or implants relative to the bone. The placed Kirschner wires are preferably used after removal of the accessory in order to position the bone parts relative to each other after sawing so that the implant can be fixedly screwed. The Kirschner wires in this way provide a mechanism for handling the bone parts, which are detached from each other after sawing.

The step of sawing the bone preferably comprises of making two saw cuts via the respective guides of the accessory and removing a bone segment between the saw cuts. The bone is in this way shortened.

The Kirschner wires are preferably removed after fixedly screwing the implant. After the implant has been fixedly screwed, the Kirschner wires no longer have any function because the implant can no longer move relative to the bone after being fixedly screwed.

The invention will now be further described on the basis of an exemplary embodiment shown in the drawing.

In the drawing:

FIG. 1 shows a top view of an implant and an accessory from a set according to an embodiment of the invention;

FIG. 2 shows a cross-section of an implant and a plurality of accessories from a set according to a further embodiment of the invention.

The same or similar elements are designated in the drawing with the same reference numerals.

Figure 3A:
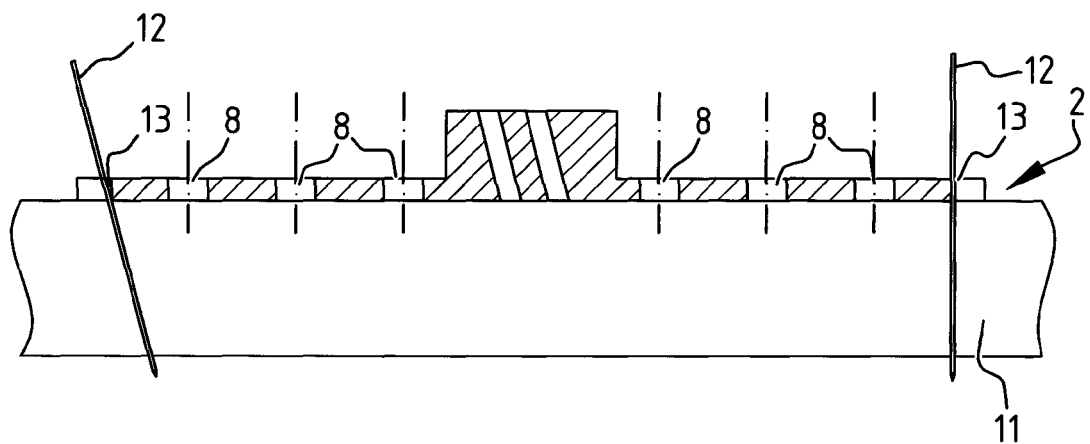
FIG. 3 shows steps for performing an osteotomy making use of a set according to a further embodiment of the invention.

FIG. 1 shows a set for performing a bone-shortening osteotomy of a predetermined distance. The set comprises an implant 1 and an accessory 2. Implant 1 is typically a bone shortening plate which functions as osteosynthesis material. Implant 1 is typically manufactured from titanium. Implant 1 has a proximal segment 3 and a distal segment 4. When implant 1 is formed symmetrically, distal and proximal segments can be interchanged.

The terms proximal and distal define an anatomical direction. An anatomical direction typically departs from the centre of the body of a person. The term proximal designates here the direction toward the centre of the body, while the term distal designates the direction away from the centre of the body. When an accessory or an implant is placed on a bone, the implant can be defined making use of this anatomical direction. The implant from the set according to the invention is intended here to extend over a saw cut in a bone. Two parts of the implant are placed on different sides of the saw cut. In the description of the present invention the terms proximal and distal are therefore used in similar manner to describe the implant relative to the saw cut.

Accessory 2 has a first segment 5, a second segment 6 and a third segment 7. First segment 5 has the same shape as proximal segment 3 of implant 1. Third segment 7 of accessory 2 has the same shape as distal segment 4 of implant 1. It will be apparent to the skilled person that accessory 2 can also be manufactured symmetrically, whereby first segment 5 also corresponds to distal segment 4 of the implant and third segment 7 also corresponds to proximal segment 3 of the implant. Accessory 2 is typically manufactured from a plastic material. The accessory can alternatively also be manufactured as non-disposable from a metal such as stainless steel, titanium or cobalt chrome.

Implant 1 always comprises at least two threaded holes at the position of its proximal segment 3 and at the position of its distal segment 4. Proximal segment 3 comprises at least two threaded holes and distal segment 4 also comprises at least two threaded holes. In FIG. 1 three threaded holes 8 are provided in proximal segment 3 and three threaded holes 8 are provided in distal segment 4 (so six in total). Because first segment 5 of accessory 2 has the same shape as proximal segment 3 of implant 1, first holes 9 are present in first segment 5 which correspond to threaded holes 8 in proximal segment 3 of implant 1. This means that the same number of holes 9 are provided in first segment 5 of accessory 2 as in proximal segment 3 of implant 1. According to a first embodiment, the holes in accessory 2 have the same size, the same shape and are placed at the same position relative to each other as threaded holes 8 in proximal segment 3. According to a further embodiment, the holes have the same relative position on the accessory and the implant but they do not have the same size or shape. A drill guide, which enables drilling at precisely the correct position, then fits in the holes on the accessory. The shape is further chosen such that, when the screw length is measured, the screw fits into the accessory to the same depth as the screw into the implant in order to correctly measure the length. Threaded holes on standard implants can in practice be oval, so do not correspond in respect of shape to the threaded holes on the accessory, since drilling of the drilled hole would then not always take place at the ideal position. Accessory 2 has at least at the position of the holes, and preferably over the whole first segment 5, the same thickness (or the same thickness profile) as proximal segment 3 of implant 1. First segment 5 of accessory 2 is hereby shaped, at least at the position of the holes, as a substantially identical three-dimensional copy of proximal segment 3 of implant 1.

Third segment 7 of accessory 2 has the same shape as distal segment 4 of implant 1. The description above, which describes the relation between first segment 5 and proximal segment 3, can likewise be applied to the relation between third segment 7 and distal segment 4. Third segment 7 of the accessory hereby forms, at least at the position of the holes, a substantially identical three-dimensional copy of distal segment 4 of implant 1.

A second segment 6 is situated between first segment 5 and third segment 7 of accessory 2. Second segment 6 comprises guides 10 for guiding a saw blade when the osteotomy is performed. The distance between the two guides 10 in second segment 6 of accessory 2 is such that an osteotomy of a predetermined distance can be performed. This means that, when an osteotomy of 3 mm has to be performed, guides 10 are formed so as to guide a saw blade such that sawing of the bone via a saw guided through guides 10 has the result that the 3 mm of bone is sawn away. For a saw with a thickness of 1 mm, the two guides will for instance in practice be placed 2 mm apart (centre-to-centre). When an osteotomy is performed via such guides, with a centre-to-centre intermediate spacing of 2 mm and a saw thickness of 1 mm, 3 mm of bone will be removed. The skilled person will appreciate how such guides have to be placed relative to each other, taking into account the saw thickness and the angular position of guides 10 relative to the bone, in order to be able to perform an osteotomy of a predetermined distance.

Each of the guides 10 is formed as a channel. This channel is formed in a block-like portion of the accessory which forms second segment 6 and which connects first segment 5 to third segment 7. In this block the channels are provided with at least two opposite surfaces between which the saw blade can move. The surfaces typically have an intermediate spacing substantially equal to or slightly greater than the thickness of the saw blade, such that the saw blade can move between the surfaces. The channel is thereby formed such that the saw blade is guided in a predetermined saw cut.

Accessory 2 and implant 1 are further formed relative to each other such that the distance between first segment 5 and third segment 7 of the accessory is equal to the sum of the predetermined distance of shortening (determined by the intermediate spacing of guides 10 in second segment 6 of the accessory) and a corresponding spacing between proximal segment 3 and distal segment 4 of the implant. It will be apparent here that the distance between proximal segment 3 and distal segment 4 can be measured in different ways, but that these differences are fully compensated in that the distance between first segment 5 and third segment 7 of accessory 2 is measured in a corresponding manner. Because proximal segment 3 corresponds to first segment 5 and because distal segment 4 corresponds to third segment 7, a corresponding measurement can be performed by the skilled person. The distance between the centre of the most proximal threaded hole 8 of proximal part 3 and the centre of the most distal threaded hole 8 of distal part 4 can thus be compared for instance to a corresponding distance on the accessory as measured between the centre of a hole in first segment 5 furthest removed from the middle of accessory 2 and a centre of a hole in third segment 7 furthest removed from the middle of accessory 2. The distance between the first segment and the third segment in accessory 2 is then equal to the sum of the corresponding distance between proximal segment 3 and distal segment 4 of implant 1 increased by the predetermined distance of osteotomy (which is determined by guides 10 of accessory 2).

As alternative to using the second segment of the accessory to make the saw cuts, a separate saw with two saw blades can also be used, wherein the saw forms part of the set. The two saw blades lie parallel here at a predetermined distance from each other. This separate saw is then used after drilling of the holes with the accessory and optionally after removal of the accessory. The separate saw is chosen here such that the distance between the two saw blades is such that the pre-desired bone resection (shortening) is performed which corresponds to the accessory from the set. If a shortening of 3 mm is thus planned, the appropriate accessory for a 3 mm shortening is used to drill the holes, and then the appropriate saw for removing 3 mm of bone. When the two saw blades have a thickness of 0.4 mm, a bone fragment of 2.2 mm is thus typically removed. Together with the two cuts of 0.4 mm, this produces a bone resection of 3 mm.

FIG. 2 shows a further set according to a further embodiment of the invention. In the set of FIG. 2 one implant 1 is provided and three accessories are provided, i.e. accessory 2A, 2B and 2C. Each of the accessories 2A, 2B, 2C is provided here for an osteotomy of a different distance. Accessory 2A can thus be provided so as to perform an osteotomy of 3 mm, while 2B can be provided so as to perform an osteotomy of 5 mm, while accessory 2C is provided so as to perform an osteotomy of a distance of 7 mm. The skilled person will appreciate that an accessory can be provided for any distance and that the above stated distances are only examples. Each of the accessories 2A, 2B, 2C has the same shape here as the one implant 1. This allows a surgeon to select an accessory from the different accessories 2A, 2B, 2C in order to perform an osteotomy of the corresponding distance. This choice of accessory is made by the surgeon on the basis of knowledge and experience, and making this choice does not form part of the invention. The set according to the invention does however allow possible choices. The different distances are implemented in the respective accessories, on the one hand by positioning guides 10 at a different distance from each other and also by modifying the distance between first segment 5 and third segment 7 (relative to a corresponding distance in the implant) to the distance between guides 10.

FIG. 3 shows the method for performing an osteotomy of a predetermined distance making use of the set according to the invention. Explained here in the description of FIG. 3 is a medical method, although advantages and effects of the set according to the invention are also explained. This is because several of these advantages and effects are a direct result of technical choices made in the set according to the invention.

The method for performing an osteotomy begins of course with making an incision into the body part where the osteotomy is to be performed (for instance the lower arm in the case an ulnar shortening is performed), and exposing the bone which has to be shortened. The surgeon determines here the distance by which a bone has to be shortened. An accessory from the set according to the invention can be selected subject to this determined distance (see FIG. 2 and associated description).

FIG. 3A shows how the selected accessory 2 is positioned relative to bone 11. Kirschner wires 12 can be used in the positioning of accessory 2 relative to bone 11. Kirschner wires 12 are generally known in surgery for positioning accessories and/or implants relative to the bone. Kirschner wires are also used to secure different bone parts relative to each other. Accessory 2 can for this purpose comprise Kirschner wire openings 13. At least one Kirschner wire opening 13 is preferably provided in each of the first segment 5 and third segment 7. A plurality of Kirschner wire openings 13 are more preferably provided in each of the first segment 5 and third segment 7. The implant can have corresponding Kirschner wire openings here, although this is not essential in the broadest embodiment of the invention. It will however be apparent that the more the Kirschner wire openings 13 of accessory and implant correspond, the more use can be made of positioning and fixation by means of the Kirschner wires. When Kirschner wire openings 13 are provided in accessory 2, corresponding Kirschner wire openings 14 are preferably provided in the implant (see FIG. 3F). The Kirschner wire openings 14 in implant 1 are then positioned relative to threaded holes 9 in the same way as Kirschner wire openings 13 in accessory 2 which are positioned relative to the first and second holes 8.

Figure 3B:
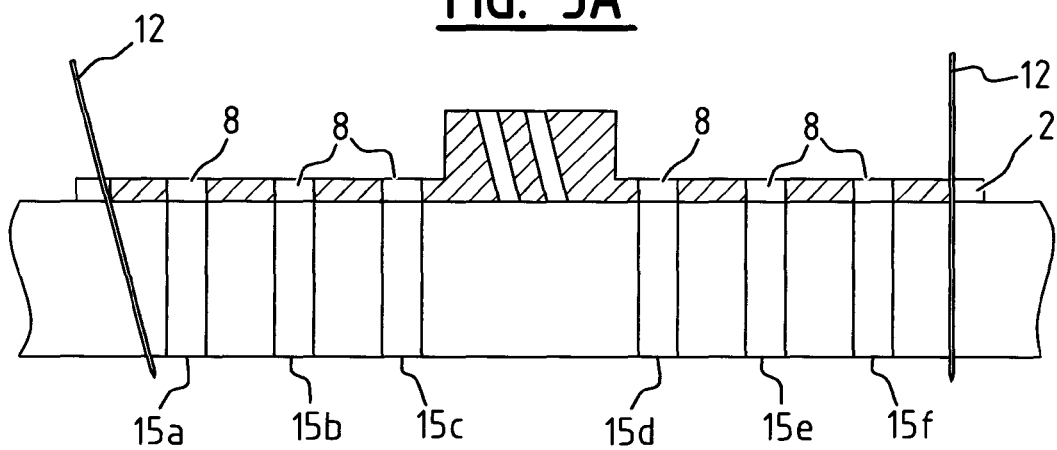

Once accessory 2 has been positioned relative to bone 11 by means of Kirschner wires 12, holes are drilled in bone 11 via the first and second openings 8. The sequence in which the holes are drilled is not important here. All holes can be drilled, though this is not necessary. At least one hole is drilled proximally and distally of the osteotomy. Surgeons wishing to use locking screws (screws with a head comprising screw thread which fits into screw thread in the implant and so provides a more stable fixation construction), and if the implant is suitable therefor, can drill one or more holes after fixing of the implant. Holes for locking screws are typically drilled by rotating a drill guide into the hole of the implant so that drilling takes place in precisely the correct direction. Alternatively, there are also variable angle locking screws, wherein the direction of drilling is less critical (15° tolerance usually possible). Drilling of the holes in bone 11 is shown in FIG. 3B. In the shown example a hole is drilled in the bone for each of the openings 8, in the example of FIG. 3B three proximal holes 15a, 15b and 15c are drilled, and three further distal holes 15d, 15e and 15f are drilled. The length of each screw must be precisely determined for the purpose of securing accessory 2 and/or implant 1 relative to the bone. This is generally known in surgery and has to do with material properties of bone (which is typically soft on the inside and hard at the position of the outer shell). The length of the screw depends on the thickness of accessory 2 and/or implant 1 at the position of the hole and on the length of the hole through the bone. Because accessory 2 has the same shape as implant 1 at least at the position of holes 8, the lengths of the screws which will be used at the end of the medical method to secure implant 1 relative to the bone can already be determined via the accessory when bone 11 has not yet been sawn through. Screw lengths can hereby be exactly determined more easily, and fewer complications will occur during securing of implant 1. This is because, since the bone has not yet been sawn through, the fixation of accessory 2 relative to bone 11 is precise and relatively strong. This makes it possible to determine the screw lengths in simple manner.

Figure 3C:
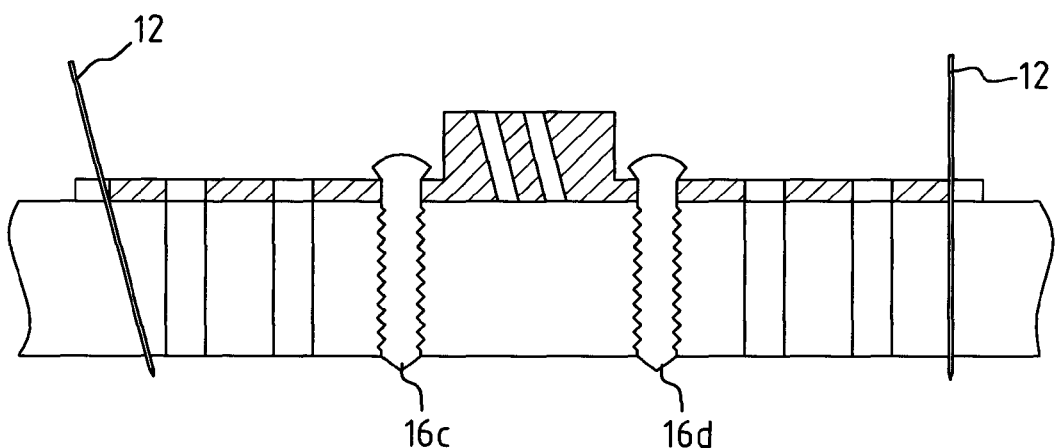

Once holes 15 have been drilled into the bone and once the screw lengths have been determined for fixedly screwing accessory 2 and/or implant 1 to the bone in each of the respective holes, accessory 2 is screwed at least partially to the bone. In FIG. 3C this is done by placing the screws which are adjacent to second segment 6. In the example of FIG. 3C these are screws 16c and 16d. The lengths of these screws were determined in the previous step. Because in the example of FIG. 3 accessory 2 has been further fixed to bone 11 using Kirschner wires 12, accessory 2 is screwed sufficiently firmly to bone 11 by means of screws 16c and 16d. The lengths of screws 16a, 16b, 16e and 16f can optionally be determined once screws 16c and 16d have been secured. It will be apparent from the above description that the method can be performed in different ways and with different sequence of steps, and that this step is only an example.

Figure 3D:
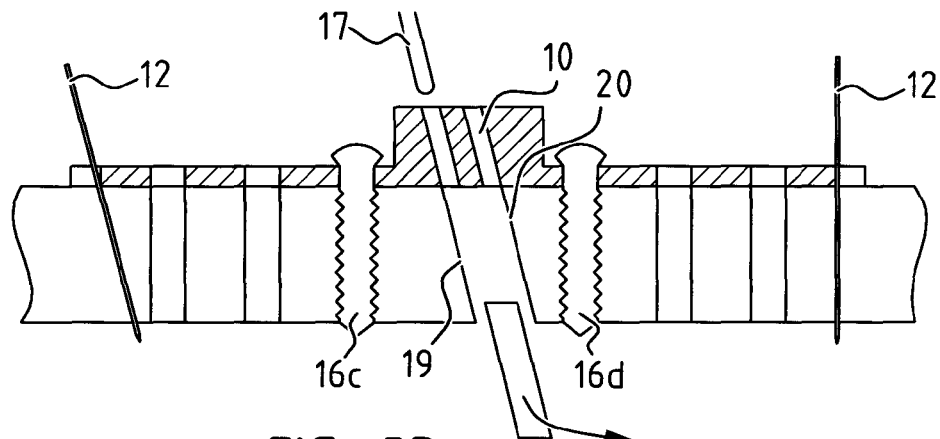

In a subsequent step, shown in FIG. 3D, the effective osteotomy is performed. Specifically, a saw blade 17 is moved in each of the guides 10 in order to saw through bone 11. Two saw cuts 19 and 20 are obtained via the two guides 10 of accessory 2. The bone segment 18 extending between the two saw cuts 19 and 20 is removed. Because saw 17 is guided in guides 10 while sawing through bone 11, saw cuts 19 and 20 are neatly parallel to each other. This allows the bone parts which thus result after shortening to connect closely together so that a speedy recovery of the bone can take place. In the example of FIG. 3 guides 10 are placed at an angle relative to bone 11, while in the examples of FIGS. 1 and 2 the guides were positioned perpendicularly relative to bone 11. The skilled person will appreciate that each of these embodiments is possible and that a bone shortening of a predetermined distance can be performed via either of these embodiments. As described above, the saw cuts can alternatively be partially made, wherein the partially made saw cuts are completed after removal of the accessory. Since they have been partially made, the same direction can be followed accurately.

Figure 3E:
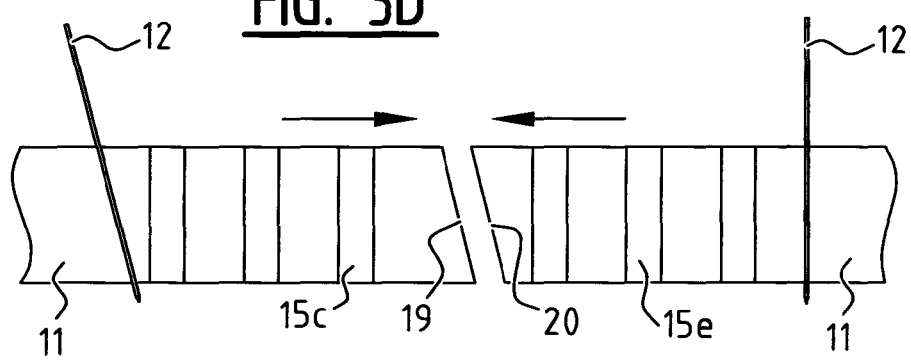
Figure 3F:
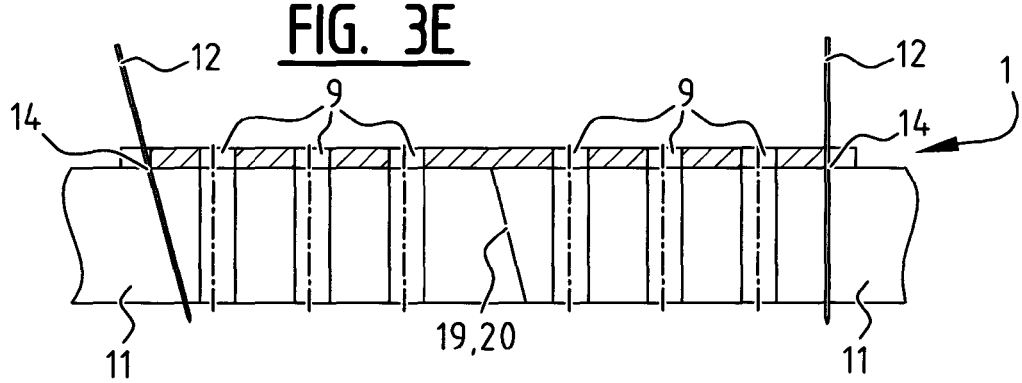
Figure 3G:
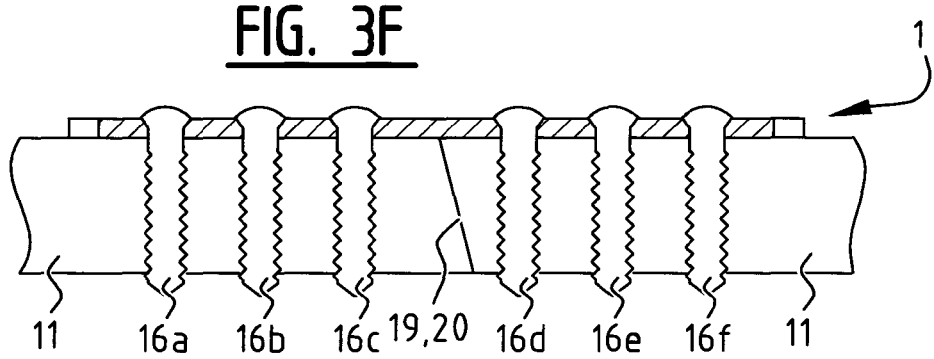

Once bone 11 has been sawn through and saw cuts 19 and 20 have been obtained, accessory 2 is removed from the bone. This is shown in FIG. 3E. The bone parts can be moved toward each other by manipulating Kirschner wires 12. These Kirschner wires form a manipulating mechanism for the surgeon for the purpose of manipulating the bone parts. Forceps can for instance thus be placed over the Kirschner wires 12 in order to pull the bone parts toward each other. Kirschner wires 12 can alternatively be manipulated manually. As further alternative, no or more than two K-wires can remain in situ, depending on the implant that will be used. It can also be an option to place a separate clamp on one or more K-wires after sliding of the implant over the K-wires in order to thus hold the implant pressed against the bone and to make the construction more stable so as to facilitate insertion of the screws.

After accessory 2 has been removed, implant 1 can be placed relative to bone 11. In the exemplary embodiment of FIG. 3 the implant has Kirschner wire openings 14. This has the advantage that, when implant 1 is placed with the Kirschner wires 12 through openings 14, the bone parts of bone 11 are automatically positioned correctly relative to each other. This means that saw cuts 19 and 20 come to lie against each other. In this position the holes formed in the bone will be aligned with threaded holes 9 of implant 1. The screws for securing the implant (screws 16a-16f) have also already been selected. This means that the surgeon need neither drill any more holes in bone 11 nor perform any measurements after positioning of implant 1. The surgeon can immediately begin securing the screws (which have already been selected) in the corresponding holes. Implant 1 can thus be secured relative to bone 11 in order to fix the bone parts relative to each other.

The above stepwise explanation of the method for performing an osteotomy shows that there are no particular conditions set for implant 1. This implant 1 can be a standard osteosynthesis plate. No markings for sawing of a predetermined distance need be provided on implant 1 (these are in the second segment of the accessory). Nor need channels in which screws can be secured at different positions be provided in implant 1, since the positions of the drilled holes correspond directly to the positions of the holes in implant 1 (owing to the specific construction of the accessory). A further advantage of the invention worthy of mention is that the implant need not be clamped fixedly relative to the bone with clamps in order to be able to determine the screw lengths. Via the accessory of the invention the screw lengths can already be determined by means of the accessory. All this allows an osteotomy to be performed in a reliable, time-efficient and cost-efficient manner since, because there are no particular set conditions for implant 1, it can be manufactured with maximum price efficiency. Accessories 2 are typically of plastic and therefore inexpensive to manufacture. The set according to the invention further allows the surgeon to work in very time-efficient manner.

On the basis of the above description, the figures and the possible alternatives stated in the text, the skilled person will appreciate that different possible configurations and embodiments can be envisaged. The description and examples given above will not be limitative for the invention, which is defined in the claims.

The invention claimed is:

1. A set suitable for use in a bone-shortening osteotomy of a predetermined distance, the set comprising:
   an implant including a distal segment and a proximal segment, wherein the distal segment comprises at least two distal threaded holes and wherein the proximal segment comprises at least two proximal threaded holes; and
   a plurality of accessories, wherein each accessory is adapted for use in a bone-shortening osteotomy of one of a plurality of predetermined distances, each accessory comprising successively a first segment, a second segment and a third segment, wherein the first segment comprises first threaded holes and wherein the third segment comprises second threaded holes, and wherein the second segment comprises two guides which are each adapted to guide a saw blade such that the bone-shortening osteotomy of the predetermined distance can be performed via the two guides, wherein the first threaded holes and the second threaded holes respectively correspond to the at least two distal threaded holes and the at least two proximal threaded holes, with an intermediate spacing between first and second threaded holes which is equal to the sum of said predetermined distance and a corresponding intermediate spacing between distal and proximal threaded holes, and wherein the first segment and the third segment have the same shape, at least at the position of the threaded holes, as respectively the distal segment and proximal segment.

2. The set as claimed in claim 1, wherein the whole first segment has the same shape as the distal segment, and wherein the whole third segment has the same shape as the proximal segment.

3. The set as claimed in claim 1, wherein the first segment has the same thickness as the distal segment, and wherein the third segment has the same thickness as the proximal segment.

4. The set as claimed in claim 1, wherein an outer surface of the first segment has the same shape as an outer surface of the distal segment, and wherein an outer surface of the third segment has the same shape as an outer surface of the proximal segment.

5. The set as claimed in claim 1, wherein the first threaded holes and the second threaded holes respectively have a position relative to each other which is the same as a position of the at least two distal threaded holes relative to the at least two proximal threaded holes.

6. The set as claimed in claim 1, wherein each guide is formed as a channel substantially defined by two surfaces which extend parallel and in which the saw blade can move in order to be guided thereby in a sawing position and in a sawing direction.

7. The set as claimed in claim 1, wherein the distal segment and the proximal segment each comprise an opening for a Kirschner wire, and wherein the first segment and the third segment each comprise a corresponding opening.

8. A method for performing a bone-shortening osteotomy of a predetermined distance, wherein the method is performed using a set from claim 1, and wherein the method comprises:
   positioning an accessory from the set relative to the bone, the accessory comprising threaded holes and comprising guides for guiding a saw;
   wherein, after positioning of the accessory, the method further comprises:
   drilling holes in the bone through the threaded holes;
   measuring each of the drilled holes in order to select for each of the holes a screw with a length suitable for fixedly screwing the accessory onto the bone;
   at least partially securing the accessory to the bone;
   sawing the bone while making use of the guides;
   after which the method comprises removing the accessory and subsequently placing an implant from the set and fixedly screwing the implant making use of the respective selected screws.

9. The method as claimed in claim 8, wherein the accessory is positioned using Kirschner wires which are placed in the bone and which extend through Kirschner wire openings of the accessory.

10. The method as claimed in claim 9, wherein the placed Kirschner wires are used after removal of the accessory in order to position the bone parts relative to each other after sawing so that the implant can be fixedly screwed.

11. The method as claimed in claim 8, wherein the step of securing the accessory to the bone is performed by screwing the accessory at least partially to the bone.

12. The method as claimed in claim 8, wherein the step of sawing the bone comprises of making two saw cuts via the respective guides of the accessory and removing a bone segment between the saw cuts.

13. The method as claimed in claim 8, wherein the Kirschner wires are removed after fixedly screwing the implant.

14. A set suitable for use in a bone-shortening osteotomy of a predetermined distance, the set comprising:
   an implant including a distal segment and a proximal segment, wherein the distal segment comprises at least two distal threaded holes and wherein the proximal segment comprises at least two proximal threaded holes; and
   a plurality of accessories, wherein each accessory is adapted for use in a bone-shortening osteotomy of one of a plurality of predetermined distances, each accessory comprising successively a first segment, a second segment and a third segment, wherein the first segment comprises first threaded holes and wherein the third segment comprises second threaded holes, and wherein the second segment comprises two guides which are each adapted to guide a saw blade such that the bone-shortening osteotomy of the predetermined distance can be performed via the two guides, wherein the plurality of predetermined distances of the plurality of accessories are provided by positioning the two guides at a different distance from each other, wherein the first threaded holes and the second threaded holes respectively correspond to the at least two distal threaded holes and the at least two proximal threaded holes, with an intermediate spacing between first and second threaded holes which is equal to the sum of said predetermined distance and a corresponding intermediate spacing between distal and proximal threaded holes, and wherein the first segment and the third segment have the same shape, at least at the position of the threaded holes, as respectively the distal segment and proximal segment.

15. A set suitable for use in a bone-shortening osteotomy of a predetermined distance, the set comprising:
   an implant including a distal segment and a proximal segment, wherein the distal segment comprises at least two distal threaded holes and wherein the proximal segment comprises at least two proximal threaded holes; and
   a plurality of accessories, wherein each accessory is adapted for use in a bone-shortening osteotomy of one of a plurality of predetermined distances, each accessory comprising successively a first segment, a second segment and a third segment, wherein the first segment comprises first threaded holes and wherein the third segment comprises second threaded holes, and wherein the second segment comprises two guides which are each adapted to guide a saw blade such that the bone-shortening osteotomy of the predetermined distance can be performed via the two guides, wherein the plurality of predetermined distances of the plurality of accessories are provided by modifying a distance between the first segment and the third segment, wherein the first threaded holes and the second threaded holes respectively correspond to the at least two distal threaded holes and the at least two proximal threaded holes, with an intermediate spacing between first and second threaded holes which is equal to the sum of said predetermined distance and a corresponding intermediate spacing between distal and proximal threaded holes, and wherein the first segment and the third segment have the same shape, at least at the position of the threaded holes, as respectively the distal segment and proximal segment.

* * * * *